United States Patent [19]

Relyveld

[11] 4,016,252

[45] Apr. 5, 1977

[54] CALCIUM PHOSPHATE GEL FOR ADSORBING VACCINES

[75] Inventor: Edgar Hans Relyveld, Paris, France

[73] Assignee: Institut Pasteur, Paris, France

[22] Filed: Dec. 11, 1975

[21] Appl. No.: 639,926

Related U.S. Application Data

[63] Continuation-in-part of Ser. No. 610,333, Sept. 4, 1975, abandoned, which is a continuation of Ser. No. 342,932, March 20, 1973, Pat. No. 3,925,545.

[30] Foreign Application Priority Data

Apr. 6, 1972 France .............................. 72.12036

[52] U.S. Cl. .................................. 424/88; 424/89; 424/92

[51] Int. Cl.$^2$ ................. A61K 39/00; A61K 39/02; A61K 39/12; A61K 47/00

[58] Field of Search ................. 252/317; 424/88–92

[56] References Cited

UNITED STATES PATENTS

| | | | |
|---|---|---|---|
| 2,605,229 | 7/1952 | Marcus | 252/317 |
| 2,967,802 | 1/1961 | Towey et al. | 424/92 |
| 3,027,229 | 3/1962 | Towey et al. | 23/109 |
| 3,608,071 | 9/1971 | Relyveld | 424/88 |
| 3,925,545 | 12/1975 | Relyveld | 424/92 |

*Primary Examiner*—Shep K. Rose
*Attorney, Agent, or Firm*—Toren, McGeady and Stanger

[57] ABSTRACT

An improved aqueous gel of calcium phosphate, useful for preparation of adsorbed vaccines, prepared by contacting an antigen with an aqueous gel obtained by reacting an aqueous solution of dibasic sodium phosphate with an aqueous solution of calcium chloride, wherein the calcium chloride solution is poured as rapidly as possible, within less than 3 minutes, into said phosphate solution, in a proportion substantially equal to 1 mol $PO_4HNa_2$ for 1 mol $CaCl_2$, under stirring; the mixture thus obtained is still stirred while its pH is adjusted to a value very near 7, and the gel formed is subsequently decanted and washed. The gel is composed of calcium and phosphate ions in proportions such that the ratio Ca/P is 1.62 to 1.85, and exhibits a settling rate of 1 to 20 mm in 10 minutes at 20° C when containing 0.07 atoms Ca per liter.

9 Claims, 1 Drawing Figure

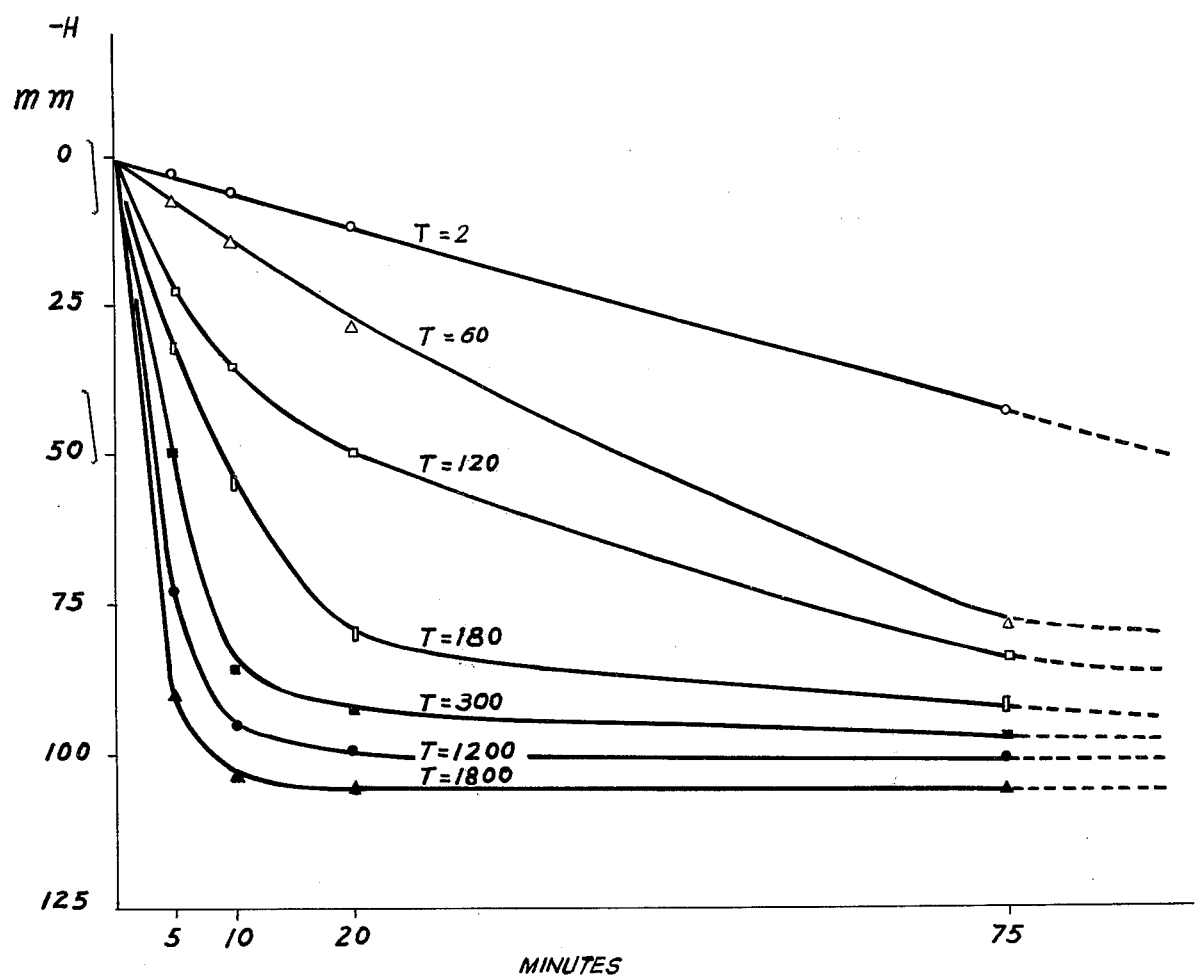

4,016,252

CALCIUM PHOSPHATE GEL FOR ADSORBING VACCINES

CROSS REFERENCE TO RELATED APPLICATIONS

This application is a Continuation-in-Part of copending application Ser. No. 610,333 filed Sept. 4, 1975, now abandoned, which, in turn, is a continuation of application Ser. No. 342,932, filed on Mar. 20, 1973, now U.S. Pat. No. 3,925,545.

BACKGROUND OF THE INVENTION

1. Field of the Invention

The present invention relates to an improved calcium phosphate gel for the preparation of adsorbed vaccines. It includes the vaccines adsorbed by a novel gel of this kind.

2. Description of the Prior Art

The advantages of adsorbed vaccines are known. The concentrated form in which they may be present provides the advantage of only requiring a small space for their storage, whilst it is possible to prepare, when needed, large quantities of vaccines in very little time from this form. This is particularly valuable in the event of epidemics or other occurrences when the vaccines might be necessary immediately. The adsorbed preparations, which remain stable for several years, enable the need for control of their dilution products to be considerably reduced, since the necessary titrations have been carried out on the concentrated products.

For these reasons, the adsorbed vaccines have been the subject of various investigations, not all of which have led to satisfactory results. In fact, the majority of adsorbants which have been proposed have the drawback that they are irritants, that they exhibit poor adsorption of the antigens, or that they are difficult to adapt to an industrial scale preparation.

Some progress has been made with the use of a calcium phosphate gel prepared by the known method of Tiselius, that is to say, a gel formed of brushite wherein the phosphate is in the form of $PO_4HCa.2H_2O$. However, even in this form, the gel does not adsorb sufficient antigens in all cases of interest and quite often its deleterious properties leave much to be desired. A further improvement has ameliorated the vaccines adsorbed on calcium phosphate gel, i.e., the one which forms the subject of Belgian Pat. No. 721,141 or U.S. Pat. No. 3,608,071 and which consists of precipitating the phosphate within a medium containing the antigen. The gel still has the composition of brushite.

SUMMARY OF THE INVENTION

The present invention is an improvement in a calcium phosphate gel which results in an appreciable improvement over the adsorbed vaccines hitherto prepared. The invention enables very strongly adsorbing gels to be obtained which can lead to highly concentrated and stable vaccines, the injection of which does not cause any irritations or complications. Moreover, the novel calcium phosphate gel according to the invention can be utilized for adsorption after having been prepared and in order to preserve its good qualities, it need no longer be formed within a medium containing the antigen.

This advantage is due to the fact that the particles of the special calcium phosphate of the invention are considerably finer than those of the hitherto known and used calcium phosphate gels. For parenteral administration of suspensions it is always highly desirable that the particles of the suspension be as fine as possible. This requirement is well met by the gel of the present invention, which exhibits a marked colloidal character. The fineness of particles in the gel of the invention is demonstrated by the fact that the velocity of settling of the gel is much slower than that of conventional calcium phosphate gel.

Specifically, the present invention comprises an aqueous gel of calcium phosphate wherein the calcium and phosphate ions are in such proportions that the weight ratio Ca/P is from about 1.62 to 1.85, the rate of settling of the gel being from about 1 to 20 mm in 10 minutes when the gel contains 0.07 Ca atoms per liter.

BRIEF DESCRIPTION OF THE DRAWING

The drawing is a graph of the relationship of the sedimentation rate to the pouring time of the $CaCl_2$ solution.

DESCRIPTION OF THE PREFERRED EMBODIMENT

The process for preparing a gel of calcium phosphate of the present invention comprises mixing an aqueous solution of bisodium phosphate and an aqueous solution of calcium chloride characterized in that the solution of calcium chloride is very rapidly introduced, with continuous stirring, into the solution of bisodium phosphate. This introduction should be effected as rapidly as possible and, in any event, in less than three minutes.

The invention results from the surprising observation that the very rapid addition of the calcium salt leads to a calcium phosphate which differs from brushite and from dibasic phosphates which form when an aqueous solution of calcium chloride is gradually added, with stirring, to a solution of bisodium phosphate. In fact, the phosphate which constitutes the gel according to the invention has a chemical composition nearer to tricalcium phosphate $(PO_4)_2Ca_3$ while the phosphates which have hitherto been used for vaccine adsorption had the composition of brushite, $PO_4HCa$, or near this composition.

When the mixing is effected at the elevated rate noted above, a part of the phosphorus ions remains in solution, so that the precipitate is richer in calcium than theory would indicate, even if the proportions of the starting materials, bisodium phosphate and calcium chloride, are equimolar.

The molarity of the solutions used according to the invention may advantageously be between 0.01 and 0.5, preferred values being from 0.05 to 0.1. Within these limits, the aqueous solution of calcium chloride can have a concentration differing from that of the bisodium phosphate, but its volume is such that in the final mixture, there is substantially 1 mol of the one per 1 mol of the other of the reagents.

Although the duration of adding the calcium salt to the bisodium phosphate may be up to approximately three minutes, it is preferable for it not to exceed one minute. Excellent results are obtained when one works with such volumes that it is possible to instantly pour the aqueous solution of $CaCl_2$ into that of the bisodium phosphate. Thus, with quantities of the order of 50 liters, it is possible to perform the mixing in a time of 2 to 30 seconds.

One practical way of operating consists in placing the solution of bisodium phosphate into a container or pan equipped with stirring means and to rapidly empty into the container, the contents of a reservoir containing the corresponding volume of calcium chloride. During this operation, the stirring means are running and stirring is continued after introduction of the CaCl$_2$ has been terminated. Especially favorable results are obtained when using a vibrator, but the agitation should also be effected by means of other devices, such as, a vane stirrer or a turbomixer.

A further important characteristic of the process for making the present gel resides in an adjustment of the pH of the mixture obtained, as soon as possible after addition of the calcium chloride. At this moment, the pH is brought to a value equal to or very near 7, more particularly 6.8 to 7.2, the range 7 to 7.2 being preferred. This adjustment is made with the aid of a solution of sodium hydroxide, the preferred concentration of which is between 0.1 N and 1 N.

As mentioned above, adjustment of the pH should follow the introduction of CaCl$_2$ as quickly as possible into the aqueous solution of bisodium phosphate. In practice, it is desirable for this adjustment to take place in less than 10 minutes after preparation of the mixture. To obtain better results, it is preferred for the adjustment of the pH to be immediate, i.e., it should take place during the 30 to 90 seconds following preparation of the mixture. The above described operations are performed at temperatures which may vary between 5° and 40° C. In practice, they can be performed at ambient temperature.

The mixture is then left to stand until the clear supernatant volume reaches 80 to 90% of the total volume. This standing may be at ordinary temperature or in the freezer and it generally last from 6 to 18 hours. The supernatant liquid is then decanted.

Examination of the gel obtained and of the separated liquid shows that all of the initial calcium is to be found in the phosphate precipitate while a portion of the PO$_4$ ions remains in solution in the clear liquid accompanying the gel. This latter characteristic is an indication of a precipitate conforming to the present invention which leads to the novel phosphate gel close to tricalcium phosphate possessing the improved properties discussed above.

After decantation of th clear liquid, a 0.4% to 0.9% solution of sodium chloride in water is added to the gel, the volume of this solution being of the same order or equal to that of the decanted liquid. The whole is mixed with the aid of a vibrator and again allowed to decant. The fresh layer of clear supernatant liquid is, in turn, removed and again replaced by a similar solution of sodium chloride. This operation is optionally repeated a third time to complete the washing of the gel.

Purification of the gel of calcium phosphate is of great importance. It has, in fact, been observed that the phosphorus ions present in the solution inhibit adsorption of certain antigens. According to the present invention, adsorption is ameliorated by the elimination of these ions. This elimination is advantageously realized by the above describing washing of the gel with a saline solution. Preferably, the washing is effected by dilution with an aqueous solution of NaCl followed by decantation. The operation is repeated several times if necessary. It is particularly recommended to use a solution of NaCl containing 4 to 9 g of this salt per liter. In fact, the final dilution of the vaccine with such a solution is favorable to the action of the vaccine.

The thus washed final gel generally contains an amount of phosphate such that its phosphorus content per liter is from 0.3 to 1.5 g and preferably from 0.7 to 0.85 g. The overall chemical analysis carried out leads, for the phosphate of the gel, to a composition between those of dicalcium and tricalcium phosphates. In fact, one finds molar ratios Ca/PO$_4$ varying between 1.20 and 1.45 and mainly between 1.25 and 1.38 which corresponds to weight ratios Ca/P of 1.55 to 1.90 and mainly 1.62 to 1.85. Since the ratio Ca/P by weight of brushite, PO$_4$CaH.2H$_2$O is 1.29 and that of (PO$_4$)$_2$Ca$_3$ is 1.98, it is apparent that the overall composition of the phosphate of the gel according to the invention lies in the neighborhood of PO$_4$CaH(PO$_4$)$_2$Ca$_3$ wherein the Ca/P is 1.72 (molar ratio Ca/PO$_4$ = 1.33). It generally contains from about 90 to 100 percent by weight of this particular phosphate.

The gel obtained is sterilized in an autoclave at 120° C for one hour whereafter the pH is adjusted to 6.8 to 7.2 and, preferably, in the range of 7 to 7.2 so as to correct the lowering of the pH towards approximately 6.5 which occurs during sterilization. It is now ready to serve as an adsorbent for various antigens in a manner known per se. It is to be well understood that the term antigen in the present invention includes all kinds of substances of microbial secretion, for example the toxoid, as well as whole micro-organisms, such as, bacteria, viruses or others, or certain of their fractions.

It has been noticed that with the precipitated phosphates according to the invention, it is possible to make the gel adsorb one or several different antigens even when this gel has already previously adsorbed another antigen. Thus the present invention comprises also the preparation of mixed vaccines by the addition of a calcium phosphate gel which has adsorbed a specific antigen, to a solution containing one or several other antigens.

If the rule of precipitation according to the present invention are followed, one or several kinds of antigens may be present in the precipitation medium, more particularly, in the starting solution of bisodium phosphate; thus a gel containing adsorbed antigens is directly obtained. After separation of the mother liquors and washings, this gel is capable of additionally adsorbing other antigens. It is thus possible to obtain mixed adsorbed vaccines by successive operations, the first of which is an adsorption in situ during the precipitation and the second an adsorption on the already formed gel.

The invention is illustrated, without limitation, by the examples which follow.

EXAMPLE 1

Preparation of adsorbed inactivated polio virus vaccines.

To 50 l of an 0.07 M solution of bisodium phosphate, continually stirred by means of a vibrator, 50 l of an 0.07 M solution of calcium chloride are added in 28 seconds; the pH of the mixture is adjusted to 7.1 with a solution of normal sodium hydroxide, following the addition of the CaCl$_2$. The 100 l of calcium phosphate gel thus obtained are left to stand until decantation of 85 l of liquid. The clear supernatant liquid is separated by siphoning and replaced by 85 l of aqueous solution of NaCl, 4 g/l.

A second washing is then effected by decantation of the saline liquid and a further addition of 85 l of 4 g NaCl per liter of water. The 100 l of suspension obtained are sterilized at 120° C whereafter their pH is adjusted to 7. The product is left standing and then 85 l of supernatant liquid are decanted.

To 15 l gel remaining at the bottom of the vessel, 100 l of an aqueous solution of antipoliomyelitis vaccine are added. The mixture is stirred for 30 minutes with the aid of a vibrator and the 115 l of product are then left standing until decantation of 100 l of clear supernatant. The latter is separated which leaves 15 l of a suspension of the calcium phosphate gel having the adsorbed antipoliomyelitis vaccine.

To the latter volume, a further portion of 100 l of vaccine is added as on the first occasion. After vibration for 40 minutes, a further decantation of 100 l liquid is performed.

To 15 l of suspension of phosphate gel charged with antigens of poliomyelitis remaining after the decantation, a third portion of 100 l of the same antipoliomyelitis vaccine is added in the manner described previously. After vibration for an additional 45 minutes, the product is left to stand and 100 l of supernatant liquid are decanted, leaving 15 l of gel suspension.

The latter thus results from 3 successive adsorptions of vaccine and constitutes a product with a high concentration of the vaccine. It should be noted that in the course of the above mentioned decantation, the supernatant was always inactive which proves that the vaccine had been completely adsorbed.

To the 15 l of suspension finally obtained, a solution of 85 l of 4 g/l NaCl containing 25 p.p.m. hyamine is added. The mixture is again agitated by means of a vibrator and after standing 85 l of liquid are decanted. To the 15 l of finally obtained gel, 85 l of a 4 g/l NaCl solution containing 25 p.p.m. hyamine are added. The resultant vaccine is three times as concentrated as the initial vaccine and it is free of constituents of the culture medium.

As to the contents of the calcium phosphate, the corresponds in the 100 l of final product to 0.897 g/l of elementary phosphorus and 1.5 g/l of calcium. Thus, the weight ratio Ca/P is 1.68 (atomic ratio 1.292) in the final gel, while at the beginning, 1 mol $CaCl_2$ has been used per 1 of $PO_4HNa_2$, i.e., weight ratio Ca/P 1.29 (atomic=1). In fact, while all the Ca has precipitated, a part of the phosphorus ion remained in solution in the eliminated supernatant and 0.31 g of P per liter of clear liquid of the first decantation were actually found.

EXAMPLE 2

Preparation of an anti-rabies vaccine.

The operations performed are the same as those of Example 1, but the antipoliomyelitis vaccine is replaced by a viral suspension obtained by culture on sheep's brain. First, a homogeneous suspension of brain containing the virus is prepared by grinding or by any other method. After the last decantation of supernatant liquid, the latter is replaced by a solution of 9 g/l of sodium chloride.

Similar preparations are obtained by culture of the virus on the brain of suckling mice or by cellular culture.

EXAMPLE 3

Preparation of a mixed vaccine.

First a suspension of calcium phosphate is prepared in situ in a soluton containing anti-diphtheria and anti-tetanus vaccines. The 100 l of suspension thus obtained are left to stand until four-fifths of the liquid is decanted and then the clear supernatant liquid is removed. To the remaining suspension of gel, 100 l of antipoliomyelitis vaccine solution are added and the whole is stirred for 30 minutes with the aid of a vibrator. After standing to decant, the supernatant liquid is again separated. Then a further volume of 100 l of the solution of inactivated polio-virus vaccine is added, stirring is renewed for half an hour and one decants so as to finally have no more than 20 l of product (this operation may be repeated several times), which is then completed with 80 l of 4 g/l NaCl containing 25 p.p.m. hyamine.

EXAMPLE 4

Preparation of a mixed vaccine.

Following the procedure of Example 1, there are prepared 25 l of anti-diphtheria vaccine adsorbed on calcium phosphate, 4 times concentrated, 25 l of anti-tetanus vaccine of the same kind and concentraton and 25 l of similar inactivated polio virus vaccine. The three volumes of 25 l are mixed and 25 l of calcium phosphate gel obtained as in Example 1 are added to the mixture. The result is a composite antidiphtheria-antitetanus-antipoliomyelitis vaccine adsorbed on calcium phosphate gel.

In another similar operation, the 25 l of phosphate gel are replaced by 25 l of pertussis vaccine adsorbed on calcium phosphate, 4 times concentrated. A quadruple composite vaccine is thus obtained.

EXAMPLE 5

Mixture with a lyophilised vaccine.

In this preparation, 50 l of gel suspension which has adsorbed anti-diphtheria and anti-tetanus vaccines prepared according to one of the preceding examples are employed for dissolving a lyophilised vaccine. The latter consists of 50,000 doses of lyophilised live attenuated measles vaccine. After dissolution of the lyophilised vaccine, the mixture is ready to be injected.

EXAMPLE 6

Improving an anti-whooping cough vaccine.

Anti-whooping cough vaccines frequently contain, even after washing, baceteria, noxious substances which are badly adsorbed and which, after injection into the organism, can cause secondary reactions. These noxious substances can, moreover, be secreted by the germs during ageing of the vaccine. In order to obviate these drawbacks, the calcium phosphate gel having adsorbed anti-whooping cough vaccine is washed in the following manner.

100 ml of suspension of the adsorbed vaccine are left in a cool chamber for 48 hours. All the clear supernatant liquid is removed and replaced by a saline solution of 9 g NaCl per liter containing a suitable doese of antiseptic. The yellowish supernatant which has been eliminated contained noxious substances. Thus, its replacement by the saline solution has rendered the vaccine far more safe and inoffensive.

In another similar preparation, the initial suspension was left in a cool chamber for 5 weeks. Thereafter the above described treatment was carried out. In this manner, the treatment has not only eliminated the noxious substances which were initially present but also those which the adsorbed microbes had secreted during the 5 weeks of ageing.

EXAMPLE 7

Four preparations of anti-diphtheria vaccine are made under conditions analogous to those of Example 1, the anti-poliomyelitis vaccine solution being replaced by that of diphtheria toxoid. In each case, one works with 1 liter of bisodium phosphate solution of 0.07 to 0.0735 M concentration containing the toxoid and 1 liter of 0.07 to 0.0735 M $CaCl_2$ solution. The latter is poured into the former with stirring over a period which differs for each of the operations A to D.

A . . . 10 seconds
B . . . 10 minutes
C . . . 20 minutes
D . . . 30 minutes

Following precipitation of the calcium phosphate, the pH of the aqueous suspension obtained is measured and then brought to the identical value of 6.85 in each of the four cases by addition of N NaOH.

The results of determinations of the speed of decantation and of various analyses performed on the suspensions A to D are given below.

pH adjustment of calcium phosphate suspensions.

TABLE I

| Preparation | pH at the end of precipitation | ml of N NaOH required per liter of suspension to bring the pH to 6.85 |
|---|---|---|
| A | 5.7 | 14.8 |
| B | 6.5 | 1.2 |
| C | 6.0 | 7.0 |
| D | 6.05 | 5.2 |

It is apparent that the suspension obtained by an extremely rapid precipitation (A) has the lowest pH.

After adjustment of the pH, the speed of decantation is measured on 50 ml of each of the suspension A to D after being stirred again. These measurements are effected at 20° C in graduated test tubes of 124 mm height (2.5 mm height per ml of capacity). The following levels of clear decanted liquid are found after the interval indicated in Table II.

TABLE II

| Times | Level in mm of decanted liquid as function of time | | | |
|---|---|---|---|---|
| | A | B | C | D |
| 5 minutes | 2.5 | 48 | 48 | 57 |
| 10 minutes | 3.8 | 82 | 83 | 89 |
| 20 minutes | 6.3 | 92 | 91 | 95 |
| 1 h 15 min | 21.2 | 100 | 95 | 105 |
| 17 hours | 85.0 | 105 | 105 | 109 |

It follows from these measurements that the speed of sedimentation of the suspension (A) of the invention is much slower than that of suspension (B, C, D) prepared in a conventional manner, i.e., by progressive addition of $CaCl_2$ to a solution of bisodium phosphate. The decantation of the suspension A is roughly 20 times slower than that of suspension B, C or D during the first 10 minutes.

Other tests have led to the observation that, according to the invention, the gels of calcium phosphate have improved qualitites when their aqueous suspensions, substantially 0.035 molar (about 1.4 g Ca/l and 1.08 g P/l) decant from 1 to 20 mm, and preferably from 2 to 10 mm, during the first ten minutes at 20° C. Vaccines which are particularly well adsorbed and easy to inject are obtained with suspensions of type A decanting no more than 6 mm in 10 minutes.

The sedimentation rates of gel A of Table II have virtually not varied after one or two washings, by decantation, of this gel with a solution of 4 g NaCL per liter water.

Adsorption capability.

Having adsorbed diphtheria toxoid during their above described preparation, the suspensions of gels A, B, C, D each titre 120 flocculation units (Uf) per ml. Following their sedimentation, their activity is determined by the flocculation method of Ramon, on the decanted liquid, which gives the following results:

A . . . 0
B . . . 50 Uf/ml
C . . . 5 Uf/ml
D . . . 7.5 Uf/ml

It can thus be seen that the phosphates B, C and D leave unadsorbed toxoid (5 to 50 Uf/ml) while the gel according to the invention adsorbs it integrally.

On the other hand, washing of the gel A by decantation with an aqueous solution of 4 g NaCl per liter does not cause the appearance of the toxoid in the saline solution, either after one or two washings.

Contents of Ca and P in the gels obtained.

Analyses of the whole suspensions A to D, of the decanted liquids and of the gels themselves have produced the results tabulated in Table III. In this table, the contents of Ca and P are expressed in g/liter. That is to say, on the one hand for the stirred, entire suspension as obtained after precipitation and adjustment of the pH to 6.85 and on the other hand, for the clear liquid separated from the precipitated phosphate by decantation, and, finally, for a suspension brought back to its initial volume by replacing the decanted liquid by distilled water.

The Ca/P ratios in Table III are by weight.

TABLE III

| | | A | B | C | D |
|---|---|---|---|---|---|
| Time of $CaCl_2$ addition during precipitation | | 10 sec. | 10 mn | 20 mn | 30 mn |
| Ca/P ratio of reagents utilized | | 1.32 | 1.28 | 1.28 | 1.34 |
| Whole initial suspension | Ca | 1.409 | 1.468 | 1.428 | 1.438 |
| | P | 1.070 | 1.150 | 1.120 | 1.070 |
| Decanted liquid | Ca | 0.026 | 0.068 | 0.040 | 0.046 |
| | P | 0.315 | 0.117 | 0.197 | 0.172 |
| Gel separated from its liquid and resuspended in water | Ca | 1.383 | 1.400 | 1.388 | 1.392 |
| | P | 0.755 | 1.033 | 0.923 | 0.898 |
| | Ca/P | 1.83 | 1.35 | 1.51 | 1.55 |

These results demonstrate that the very rapid precipitation (A) leads to a liquid medium containing less of Ca and many more phosphorus ions than the liquids of the conventional precipitations (B, C, D). On the other hand, the precipitated phosphate is much more rich in calcium, namely, a Ca/P ratio of 1.83 against 1.35 to 1.55. Although from the point of view of its composition, the phosphate D comes close to the lower limit (Ca/P — 1.55) of that of the invention, it nevertheless differs greatly therefrom in its physicochemical properties. Thus, it has been seen above that its decantation in 10 minutes is 89 mm, i.e., 23.5 times that of the gel A which is due to a granular structure and is detrimental to parenteral administration. It has also been seen that the adsorption capability of the phosphate D is poor.

When the gel of phosphate A has been subjected to two washings with 4 g/l NaCl in the manner described at the beginning of Example 1 and its suspension has been brought back to the initial colume, no more than 0.06 g P/liter is found in its clear liquid and the content of Ca therein is 0.03 g/l. The thus lowered concentration of phosphorus ions is no longer inconvenient since the precipitated phosphate has virtually the same composition as prior to the washings. In fact, a weight ratio Ca/P of 1.81 is found, against 1.83 prior to the washings. In the aggregate, Ca/P = 1.8 would correspond to $PO_4CaH.2(PO_4)_2Ca_3$.

Although the phosphate concentration in the vaccines according to the invention can vary within wide limits, it is generally virtually such that there are 1 to 2 g of Ca and 0.56 to 1.43 g of P per liter. However, an this is an advantage of the invention, the vaccine can be preserved in the form of a stable concentrate consistng of a phosphate gel of about 5 to 20 g of Ca and, respectively, about 2.8 to 14.3 g of P per liter.

EXAMPLE 8

The steps carried out in Example 8 hereof were repeated for each of the following vaccines: rabic virus, tetanic toxoid, inactivated polio virus, pertussis bacillus, and live attenuated measle virus. In each instance, essentially the same improved results were obtained with the gel of the present invention.

EXAMPLE 9

Calcium phosphate gels were prepared by the method described in the first paragraph of Example 1 and in Example 7 hereof. Thus, seven preparations were effected as follows.

To 1 liter of an aqueous solution of 0.07 M solution of dibasic sodium phosphate, continually stirred by means of a vibrator, 1 liter of 0.07 M aqueous solution of calcium chloride was poured within a time of T seconds, which varied from preparation to preparation. The pH of the suspension thus formed was adjusted to 6.9 by adding thereto a normal sodium hydroxide aqueous solution. Then 50 ml of the suspension were introduced into a 125 mm high graduated glass test tube (2.5 mm height per ml of capacity) and allowed to stand at 20° C for 17 hours. The height H, in millimeters, of the clear supernatant layer of solution was noted in each test, after 5 mn, 10 mn, 20 mn, 75 mn, and 17 hours of standing.

An aqueous solution of purified diphtheria toxoid was dialyzed to an aqueous solution of dibasic sodium phosphate. The thus obtained solution had a concentration of 0.07M in dibasic sodium phosphate and a flocculation activity determined by the Ramon method (due to the diphtheria toxoid) of 240 flocculation units per ml (240 Uf/ml).

Then, to 1 liter of this solution there was added 1 liter of a 0.07 M aqueous solution of calcium chloride within a time of T seconds to form a diphtheria toxoid containing phosphate gel (120 Uf/ml).

Five such operations were carried out, each with a different time T. Each of the five suspensions obtained was allowed to stand until as a result of sedimentation, a substantial amount of clear liquid was present. The flocculation activity in the clear liquid was determined by the Ramon method.

The results of the above tests are set forth in the following Tables IV and V, in which T — is the time of pouring the $CaCl_2$ solution in seconds;

H — is the height in mm of the clear supernatant liquid after a given number of minutes of sedimentation; and Uf — the activity of clear supernatant liquid, in flocculating units, after the sedimentation of diphtheria toxoid containing calcium phosphate gel.

Each of the values in the following tables is the average of three tests.

TABLE IV.

| T. seconds | Hmm after a time of sedimentation of: | | | | |
|---|---|---|---|---|---|
| | 5 mn | 10 mn | 20 mn | 75 mn | 17 hours |
| 2 | 2.6 | 5.2 | 11.6 | 43.1 | 89.0 |
| 60 | 6.2 | 13.4 | 27.6 | 77.9 | 101.0 |
| 120 | 21.5 | 36.1 | 49.0 | 84.0 | 101.1 |
| 180 | 30.7 | 54.8 | 80.2 | 92.1 | 104.8 |
| 300 | 48.3 | 85.4 | 92.9 | 96.4 | 105.0 |
| 1200 | 73.1 | 95.9 | 99.0 | 100.0 | 102.1 |
| 1800 | 89.8 | 103.2 | 104.8 | 104.8 | 105.6 |

A plot of the above data is shown in the Figure.

TABLE V.

| T. seconds | Flocculation activity Uf/ml in clear liquid |
|---|---|
| 2 | 0 |
| 60 | 0 |
| 120 | traces |
| 180 | 6 |
| 300 | 11 |

It is clear from the data of Table IV, that, when $CaCl_2$ is poured into the dibasic sodium phosphate solution within 2 to 60 seconds, the sedimentation of the gel formed is very slow in comparison with that of gels produced by usual methods (T = 300 to 1800 seconds). This fact obviously indicates that the structure of the gel is different from that of the usual gels. When the time of pouring the $CaCl_2$ is 60 to 180 sec., the sedimentation, while being somewhat quicker than for 2 to 60 sec., is still considerably slower than the usual conditions. This means, that the gel formed within 180 seconds (3 minutes) still has properties different from usual gels.

The Figure clearly shows that the slope of the left hand part of curve T = 300 sec. (5 minutes pouring) is much sharper than that of T = 180 sec. (3 minutes). From the graph it is seen that the curve T = 180 sec. constitutes a limit between the very slowly sedimenting gels (T = 2 to T = 180) and the normally sedimenting gels (T = 300 to T = 1800).

Table V. confirms the above considerations. It shows that gels produced within 2 to 60 seconds are so perfectly adsorbing that there is no toxoid in the clear supernatant liquid which forms during the sedimentation of the gel. When the pouring of the $CaCl_2$ lasts 180 seconds (3 minutes) a little flocculating activity appears in the clear liquid, although this is commercially acceptable, i.e., 6 Uf/ml versus 120 Uf/ml in the suspension.

However, with slower pouring of the calcium chloride, such as, for instance, 300 sec. (5 minutes), the flocculating activity becomes quite strong, i.e., 11 Uf/ml being near 10% of the activity of the suspension.

This means that the gel no longer exhibits the advantages of the gel of the present invention. Consequently, while T = 2 to 60 seconds gives outstanding results, commercially acceptable adsorption is still obtained with 60 to 180 seconds, and T = 180 should be considered as a limit, because above 180, the flocculating activity of the supernatant clear liquid rapidly increases.

What is claimed is:

1. An injectable aqueous gel of calcium phosphate for adsorbing vaccines, wherein calcium and $PO_4$ ion are combined in such proportions that the weight ratio Ca/P is from 1.62 to 1.85, the settling time of the gel when containing 0.07 atom Ca per liter, being from 1 to 20 mm in 10 minutes at 20° C.

2. The aqueous gel of claim 1 which contains 1 to 20 grams of Ca with 0.56 to 14.3 grams P.

3. The aqueous gel of claim 1 wherein wherein the calcium phosphate contains 90 to 100% by weight of $PO_4HCa \cdot (PO_4)_2Ca_3$.

4. The aqueous gel of claim 2 which contains diphtheria toxoid adsorbed by the gel.

5. The aqueous gel of claim 2 which contains rabic virus adsorbed by the gel.

6. The aqueous gel of claim 2 which contains tetanic toxoid adsorbed by the gel.

7. The aqueous gel of claim 2 which contains inactivated polio virus adsorbed by the gel.

8. The aqueous gel of claim 2 which contains pertussis bacillus adsorbed by the gel.

9. The aqueous gel of claim 2 which contains live attenuated measle virus adsorbed by the gel.

* * * * *